United States Patent [19]

Mueller et al.

[11] Patent Number: 5,134,235
[45] Date of Patent: Jul. 28, 1992

[54] PROCESS FOR SEPARATING FOLINIC ACID

[75] Inventors: Hans R. Mueller, Schaffhausen; Martin Ulmann, Dachsen; Josef Conti, Schaffhausen, all of Switzerland; Gunter Muerdel, Tengen-Busslingen, Fed. Rep. of Germany

[73] Assignee: Eprova A.G., Schaffhaussen, Switzerland

[21] Appl. No.: 668,681

[22] PCT Filed: Apr. 22, 1988

[86] PCT No.: PCT/EP88/00341
§ 371 Date: Dec. 23, 1988
§ 102(e) Date: Dec. 23, 1988

[87] PCT Pub. No.: WO88/08843
PCT Pub. Date: Nov. 17, 1988

Related U.S. Application Data

[63] Continuation of Ser. No. 294,631, Dec. 23, 1988, abandoned.

[30] Foreign Application Priority Data

May 15, 1987 [CH] Switzerland ............... 01883/87

[51] Int. Cl.⁵ ............................................. C07D 475/04
[52] U.S. Cl. ...................................................... 544/258
[58] Field of Search .............................. 544/258, 261

[56] References Cited

U.S. PATENT DOCUMENTS

| | | | |
|---|---|---|---|
| 2,688,018 | 8/1954 | Cosulich | 544/258 |
| 4,959,472 | 9/1990 | Wood et al. | 544/258 |
| 5,006,655 | 4/1991 | Mueller et al. | 544/258 |
| 5,010,194 | 9/1991 | Mueller et al. | 544/258 |

FOREIGN PATENT DOCUMENTS

| | | |
|---|---|---|
| 0266042 | 5/1988 | European Pat. Off. . |
| 305574 | 2/1955 | France . |
| 649550 | 5/1985 | Switzerland . |

OTHER PUBLICATIONS

Kanegafuchi, Chem. Abstr. vol. 98 entry 215624r (1983).
Temple et al. Cancer Treat Rep vol. 65 pp. 1117-1119 (1981).
Chem. Abstr. vol. 107 entry 214060w (1987).
Merck Index 10th Edition (1983) entry 4111.
J. Feeney, Biochemistry, vol. 20, pp. 1837-1842 (1981).
Cosulich, Jour. Am. Chem. Soc. vol. 74, pp. 4215-4216 (1952).
G. Mozzi et al., "Stabilita del calcio folinato in soluzioni acquose in funzione del pH e della temperatura", Belletino Chemico Farmaceutico, 125 (12), 1986, pp. 424-428.
Temple et al., Journal of Medicinal Chemistry, 1979, vol. 22, No. 6 pp. 731-734.
Folates and Pterins, vol. 1, Chemistry and Biochemistry of Folates, pp. xiii and 99 (1984).
Kalbermattan et al., Helvitica Chemica Acta, vol. 64, Fasc. 8, Nr. 266, p. 2627 (1981).
The Journal of Biological Chemistry, vol. 238, No. 4, pp. 1498-1500 (Apr. 1963).
Rees et al., Tetrahedron, vol. 42, No. 1, pp. 117-136 (1986).
White et al., The Journal of Biological Chemistry, vol. 253, No. 1, pp. 242-245 (Jan. 10, 1978).
Fachlexikon ABC Chemie, Stereoisomeric, p. 1077 (1987).
Analytical Biochemistry 22, 166-177 (1968).
Choi et al., Analytical Biochemistry 168, 398-404 (1988).
Fontecilla-Camps, J. C. et al., *Chemistry and Biology of Pteridines* p. 235, Elsevier/North-Holland, N.Y. (1979).
Fontecilla-CXamps et al., Journal of American Chemical Society, vol. 101:20, Sep. 26, 1979 pp. 6114-6115.
Rees, L. et al. J. Chem. Soc., Chem. Commun., *A Simple and Effective Method for the Preparation of the 6(R)- and 6(S)—Diastereoisomers*, pp. 470-472, (1987).
Russian Article: Kaplan, E. Y. et al., Biologiceskie Nauki, vol. 7, 1987, pp. 33-37.

*Primary Examiner*—Donald G. Daus
*Attorney, Agent, or Firm*—Millen, White & Zelano

[57] ABSTRACT

Preparing (6S)-folinic acid and its salts, comprising recrystallization of alkaline-earth salts of (6R,S)-folinic acid and, where necessary, liberation of the acid from the alkaline-earth folinates and/or, where necessary, conversion into the alkali salts by at least one recrystallization in the presence of a base. Calcium-, magnesium-, potassium- and sodium-(6S)-folinates and (6S)-folinic acid are prepared.

17 Claims, No Drawings

PROCESS FOR SEPARATING FOLINIC ACID

This application is a continuation of application Ser. No. 07/294,631, filed Dec. 23, 1988, now abandoned.

BACKGROUND OF THE INVENTION

The invention relates to a process for preparing (6S)-folinic acid and its salts, especially calcium, magnesium, potassium and sodium folinate.

Folinic acid is N-(5-formyl-(6R,S)-5,6,7,8-tetrahydro-pteroyl)-L-glutamic acid (5-CHO-(6R,S)-$H_4$PteGlu). N-(5-formyl-(6S)-5,6,7,8-tetrahydropteroyl)-L-glutamic acid (5-CHO-(6S)-$H_4$PteGlu) is the citrovorum factor (=growth-promoting factor for leuconostoc citrovorum).

Folinic acid contains 2 asymmetric centers. Also, due to the synthesis of the folinic acid from folic acid, N-(pteroyl)-L-glutamic acid, the optically active C atom contained in the glutamic acid group is present in the L form while the optically active C atom resulting from the hydrogenation of the double bond in the 5,6 position is present in position 6 in the racemic, (6R,S), form. Synthetic folinic acid (=leucovorin) therefore consists of a 1:1 mixture of two diastereomers.

Leucovorin is finding increasing importance as a pharmaceutical preparation for treating megaloblastic, folic-acid-deficiency, anaemia, as an antidote for intensifying the tolerance of folic acid antagonists especially of aminopterin and methotrexate in cancer therapy (leucovorin rescue) and the treatment of autoimmune diseases such as psoriasis and rheumatoid arthritis, and intensifying the tolerance of certain antiparasites, such as trimethoprim-sulphamethoxazole, in chemotherapy.

In the natural state, for example in the liver, folinic acid is found only in the S form. The biochemical action of leucovorin as a folic acid cofactor is based on its content of 5-CHO-(6S)-$H_4$PeGlu. On the other hand the inverse (R)form -5-CHO-(6R)-$H_4$PteGlu- is barely metabolized and is slowly eliminated through the urine. It is biochemically inactive. J. A. Straw et al, Cancer Research 44, 3114 (1984).

Many attempts have therefore been undertaken to separate 5-formyl-(6R,S)-5,6,7,8-tetrahydro-pteroyl-L-glutamic acid and synthesize 5-formyl-(6S)-5,6,7,8-tetrahydro-pteroyl-L-glutamic acid asymmetrically and isolate the physiologically active form. D. Cosulich et al, J. Amer. Chem. Soc. 74, 4215-16 (1952), U.S. patent Specification 2,688,018 have attempted to accomplish the separation by fractional crystallization of an alkaline-earth salt, for example the calcium or strontium salt, of 5-formyl-(6R,S)-5,6,7,8-tetrahydro-pteroyl-L-glutamic acid from an aqueous solution. The required separation cannot be realized under the conditions published by B. Cosulich et al. In the crystallization of, for example, the calcium salt of 5-formyl-(6R,S)-5,6,7,8-tetrahydro-pteroyl-L-glutamic acid from water at pH 7-8 the pure (6R,S)-form is always obtained again, which can be shown quantitatively by chromatographic analysis on a chiral HPLC column and by reference to the optical rotation. In this case it is immaterial whether the crude or pure calcium salt of 5-CHO-(6R,S)-$H_4$PteGlu is used for the crystallization; the optically pure (6R,S)-form is always recovered. Nor can separation and concentration of the (6S)-form be achieved if the supersaturated aqueous solution of alkaline-earth-(6R,S)-folinate is seeded with authentic alkaline-earth-(6S)-folinate. Until now asymmetric synthesis has therefore remained the only possibility for preparing N-(5-formyl-(6S)-5,6,7,8-tetrahydro-pteroyl)-L-9lutamic acid.

The previously known methods for asymmetric synthesis of (6S)-folinic acid are, however, not suitable for the preparation of this compound on a commercial scale. Until the present there have therefore been no commercially viable methods for the preparation of (6S)-folinic acid.

There remains, therefore, the problem of developing a simple, commercially useful and cost-effective method for preparing (6S)-folinic acid and it salts.

SUMMARY OF THE INVENTION

Surprisingly, it was found that during the recrystallization of the alkaline-earth salts of (6R,S)-folinic acid, for example of calcium-, magnesium- or strontium-N-(5-formyl-(6R,S)-5,6,7,8-tetrahydropteroyl)-L-glutamate (=alkaline-earth-(6R,S)-folinate), preferably from water, in an alkaline environment in the presence of inorganic or organic bases initially there is predominant crystallization of the (6S)-form and the content of (6S)-form in the crystalline crop can reach 85% or more.

The alkaline-earth folinate which is heavily enriched with the (6S)-form and has a high (6S)-form content can be converted into optically pure alkaline-earth-(6S)-folinate by further recrystallization, preferably from water, at an approximately neutral pH.

During the crystallization the yield can be improved by the addition of alkaline-earth ions, for example of calcium, magnesium or strontium chloride.

The subject of the invention is thus a process for preparing (6S)-folinic acid and its salts by recrystallization of alkaline-earth salts of (6R,S)-folinic acid and, where necessary, liberation of the acid from the alkaline-earth folinates and/or, where necessary, conversion into the alkali salts, which is characterized in that the recrystallization is carried out in the presence of a base.

The subject of the invention is also a process in which the crystalline crop obtained is subjected to at least one further recrystallization in the presence of a base or at an approximately neutral pH value. In accordance with a preferred embodiment the recrystallization is carried out in the presence of additional alkaline-earth ions.

Both pure alkaline-earth-(6R,S)-folinates and crude alkaline-earth-(6R,S)-folinates are suitable as the starting material for the process.

The calcium and magnesium salts of N-(5-formyl-(6R,S)-5,6,7,8-tetrahydro-pteroyl)-L-glutamic acid have become commercially available for the first time through this process.

The calcium, magnesium, strontium and barium folinates are suitable as the alkaline-earth salts of folinic acid. The calcium and magnesium salts are preferred as these can be used directly as pharmaceutical preparations after the separation has taken place while to some extent the strontium salt and above all the barium salt are subsequently converted to another, physiologically acceptable, salt.

Suitable inorganic or organic bases are: alkali hydroxides such as sodium, potassium and lithium hydroxide, alkaline-earth hydroxides such as, in particular, calcium and magnesium hydroxide, ammonia and hydrazine, water-soluble organic bases, in particular simple primary, secondary and tertiary amines, for example, methylamine, dimethylamine, trimethylamine, ethylamine, diethylamine, triethylamine, propylamine, dipropylamine, methylethylamine, aminoalcohols, for example, ethanolamine, diethanolamine, triethanolamine, propanolamine, butanolamine, dihydroxypropanolamine (2,3-dihydroxypropylamine, serinol), trihydroxybutylamine (tris-(hydroxymethyl)-aminomethane), glucamine, N-methyl-glucamine, heterocyclic amines, for example, pyrrolidine, piperidine, morpholine or piperazine.

The first recrystallization in accordance with the process according to the invention is carried out at a pH value between 8.5 and 12, preferably between 9.0 and 10.5. At a lower pH there is no significant enrichment of the (6S)-form in the crystalline crop, and at a higher pH the stability of the folinic acid is appreciably lower and also it is difficult to make the alkaline-earth salts crystallize. To remove residual quantities of (6R)-folinate from alkaline-earth-(6S)-folinate further recrystallizations can be carried out in an approximately neutral environment, for example, in the pH range from 6.5 to 8.5. During the crystallization the solubility product can be reached more rapidly by the addition of appropriate alkaline-earth ions, thus increasing the yields. The alkaline-earth ions, preferably Ca, Mg, Sr, are added in the form of any readily soluble salts, for example in the form of the chloride, or nitrate. As a rule they are used in 0.2 to 4 times the quantity of the folinate.

The subject of the invention is also the (6S)-folinates which are commercially available for the first time through the process in accordance with the invention, especially the calcium folinate and the (6S)-folinic acid and, regardless of the method of its preparation, the new magnesium salt and the new sodium and potassium-(6S)-folinates which are easily obtained from the now readily accessible alkaline-earth-(6S)-folinates, for example by double decomposition.

The magnesium-(6S)-folinate is highly important because, due to its comparatively good water solubility of more than 2 g/100 ml and its high tolerance, it forms the appropriate starting material for the preparation of injectable solutions. This applies to an even greater extent to the sodium- and potassium-(6S)-folinates. At 20° C., calcium-(6S)-folinate is capable of forming only 0.95% aqueous solutions which makes the preparation of injectable solutions more difficult.

Examples to illustrate the invention:

EXAMPLE 1

Calcium-(6S)-folinate

1. Crystallization 100 g crude calcium-(6R,S)-folinate in approximately 1 liter of warm water at 50°-60° C. are treated with 12-36 g calcium chloride ($CaCl_2.2H_2O$), adjusted to a pH of 10 at 30° C. by the addition of aqueous ammonia (25%) and allowed to crystallize at 18° C. After 18-20 hours the precipitated product is filtered off, washed with dilute calcium chloride solution and then with moistened ethanol. 41 g calcium folinate are obtained containing 88% calcium-(6S)-folinate and 12% calcium-(6R)-folinate. Optical yield 72%.

2. Crystallization 40 g crude calcium-(6S)-folinate from the first crystallization containing 88% (6S)-folinate are dissolved in water at 55°-60° C. and slowly brought to pH 6.1 with aqueous hydrochloric acid (20%) and treated with 40 to 160 g calcium chloride. The pH of the solution is adjusted to 7 to 7.5 at 55° C. by the addition of caustic soda. Seeding with authentic calcium-(6S)-folinate is carried out at approximately 35° C. and the product is allowed to crystallize at 18°-20° C.

After approximately 40 hours, the product which has crystallized out is filtered off, washed with aqueous ethanol and dried.

30.4 g calcium-(S)-folinate are obtained with an (S)-folinate content of 98%. Optical yield: 79-81%.

3. Crystallization 10 g calcium-(6S)-folinate with a (6S)-form content of 94-98% are dissolved in hot water, treated with 10 g calcium chloride and allowed to crystallize at pH 7.0 to 7.5 and 18°-20° C. After 3 to 4 days, the product is filtered off, washed with a little Water and with moistened ethanol and dried.

8 g of pure calcium-(6S)-folinate are obtained. Content of calcium-(6S)-folinate=99-100% by area

| | |
|---|---|
| Solubility in water: | 0.95 g/100 ml at 20° C. and 1.5 g/100 ml at 40° C. |
| Specific rotation $[\alpha]_D^{20} =$ | −15° (relative to anhydrous Ca salt) |

Comments:
Content of Ca.folinate: determined by HPLC against standard.
Content of (6S)-form: determined by HPLC using a chiral column (Resolvosil-BSA-7).

EXAMPLE 2

Separation of calcium-(6R,S)-folinate by Crystallization in the Presence of Various Bases

1. Recrystallization in the Presence of Bases 30 g calcium-(6R,S)-folinate are dissolved in 200-300 ml water at 50° C. and treated at 30°-40° C. with 0.5-0.6 equivalent base per mole calcium-(6R,S)-folinate.

The solution is stirred at ambient temperature for 5 to 17 hours. As a rule spontaneous crystallization takes place soon. The crystalline crop is filtered of, washed with a little 5% calcium chloride solution and with ethanol and dried. The results can be seen from Table 1.

TABLE 1

| Base | pH | Content of (6S)-form % by area | Ca-folinate.5H$_2$O % by wt | optical yield % |
|---|---|---|---|---|
| no added base | 7.5 | 50.1 | 99 | no separation |
| sodium hydroxide | 8.5 | 52 | 101 | incipient separation |
| NaOH | 10 | 80 | 96 | 70 |
| magnesium hydroxide | 10 | 72 | 97.2 | 60 |
| calcium hydroxide | 10.2 | 79 | 93.4 | 65 |
| aminobutanol | 9.6 | 71 | 96.5 | 70 |
| ethanolamine | 10 | 85 | 97.5 | 75 |
| diethanolamine | 9.7 | 75 | 97.2 | 60 |
| serinol | 9.6 | 75 | 98.2 | 75 |
| methylamine | 10 | 79 | 96.5 | 76 |
| ethylamine | 9.9 | 82 | 97.5 | 78 |
| ammonia | 10 | 84 | 98.9 | 72 |
| hydrazine | 10 | 83 | 97 | 72 |
| potassium hydroxide | 9.5 | 77 | 98.2 | 70 |

2. Recrystallization of the Crude calcium-(6S)-folinate Obtained as Specified in 1

The crude calcium-(6S)-folinate obtained as specified in the aforesaid method 1 is recrystallized from water at pH 6.5 to 7.5 with the addition of 1-4 parts calcium chloride. During this process a somewhat less soluble fraction is separated by filtration. After concentrating and cooling pure calcium-(6S)-folinate crystallizes from the filtrate.

Content of calcium-(6S)-folinate = 99.9% by area

EXAMPLE 3

Magnesium-(6S)-folinate

1. Crystallization 30 g magnesium-(6R,S)-folinate, prepared from an aqueous solution of sodium-(6R,S)-folinate by precipitation with magnesium chloride, are dissolved in hot water, treated with 100 g magnesium chloride and adjusted to pH 10 by the addition of aqueous sodium hydroxide. The solution is now cooled to 16°–18° C. with stirring.

After a few days the crude magnesium-(6S)-folinate which has crystallized out is filtered off, washed with ethanol and dried. Magnesium folinate is obtained with an (S)-folinate content of 80%.

2. Recrystallization

Pure magnesium-(6S)-folinate with an (6S)-folinate content of more than 95% of the theoretical quantity is obtained from the crude magnesium-(6S)-folinate by recrystallization at approximately neutral pH from a small quantity of water with the addition of magnesium chloride.

Solubility in water: 2.4 g/100 ml at 20° C.

EXAMPLE 4

Sodium-(6S)-folinate

An almost saturated aqueous solution of calcium-(6S)-folinate is allowed to percolate through an ion exchanger column which is filled with cation exchanger resin in the Na(+) form, for example with amberlite IR-120, Na(+) form. The eluate is concentrated. The sodium-(6S)-folinate is precipitated by the addition of ethanol. Sodium-(6S)-folinate is readily soluble in water.

Alternatively, sodium-(6S)-folinate can also be prepared by dissolving (6S)-folinic acid in the equivalent quantity of sodium hydroxide.

The (6S)-folinic acid required for this purpose is obtained as specified in example 6.

EXAMPLE 5

Potassium-(6S)-folinate

This compound is obtained by dissolving the (6S)-folinic acid obtained as specified in example 6 in the equivalent quantity of aqueous potassium hydroxide.

The potassium-(6S)-folinate can be precipitated from its concentrated aqueous solution by treatment with ethanol, isopropanol or acetone.

Potassium-(6S)-folinate is readily soluble in water.

EXAMPLE 6

(6S)-folinic acid

An aqueous solution of calcium-(6S)-folinate is treated cautiously with dilute hydrochloric acid during which the (6S)-folinic acid (=N-(5-formyl-(6S)-5,6,7,8-tetrahydro-pteroyl)-L-glutamic acid) precipitates and is recovered by filtration.

(6S)-folinic acid is barely soluble in water.

We claim:

1. A process for preparing an alkaline-earth salt of (6S)-folinic acid comprising crystallizing an alkaline-earth salt of (6R,S)-folinic acid in the presence of a base effective to provide a pH between 8.5 and 12 and to form thereby form a precipitate selectively enriched in said alkaline-earth salt of (6S)-folinic acid as compared to the concentration of an alkaline-earth salt of (6R)-folinic acid in said precipitate.

2. A process according to claim 1, further comprising subjecting the resultant crystalline crop to at least one further crystallization at an approximately neutral pH value to obtain an optically pure alkaline-earth salt of (6S) folinic acid.

3. A process according to claim 1, wherein the crystallization is carried out in the presence of excess of the same alkaline-earth ions employed to produce the alkaline-earth salt.

4. Process according to claim 2, wherein the crystallization is carried out in the presence of excess of the same alkaline-earth ions employed to produce the alkaline-earth salts.

5. A process according to claim 1, further comprising converting the alkaline-earth salt of (6S) folinic acid into an alkali salt thereof.

6. A process according to claim 1, wherein the pH is between 9.0 and 10.5.

7. A process according to claim 6, further comprising subjecting resultant crystalline crop to at least one further crystallization at an approximately neutral pH value to obtain an optically pure alkaline-earth salt of (6S) folinic acid.

8. A process according to claim 7, wherein the further crystallization is conducted at a pH of 6.5 to 8.5.

9. A process according to claim 8, wherein at least one of the crystallization and recrystallization steps is conducted in the presence of additional alkaline-earth ions.

10. A process according to claim 3, conducted with a chloride or nitrate of calcium, magnesium, or strontium.

11. A process according to claim 1, resulting in an optical yield of the precipitated alkaline-earth salt of 6(S)-folinic acid of at least 60%.

12. A process according to claim 1, resulting in an optical yield of the precipitated alkaline-earth salt of 6(S)-folinic acid of at least 70%.

13. A process for preparing an alkaline-earth salt of (6S)-folinic acid comprising crystallizing an alkaline-earth salt of (6R,S)-folinic acid at a pH between 9.0 and 12 to form a precipitate selectively enriched in said alkaline-earth salt of (6S)-folinic acid as compared to the concentration of an alkaline-earth salt of (6R)-folinic acid in said precipitate.

14. A process according to claim 13, wherein the crystallization is carried out in the presence of excess of the same alkaline-earth ions employed to produce the alkaline-earth salt.

15. A process according to claim 14, conducted with a chloride or nitrate of calcium, magnesium, or strontium.

16. A process for preparing an alkali salt of (6S)-folinic acid comprising crystallizing an alkaline-earth salt of (6R,S)-folinic acid at a pH between 9.0 and 12 to form a precipitate selectively enriched in said alkaline-earth salt of (6S)-folinic acid as compared to the concentration of an alkaline-earth salt of (6R)-folinic acid in said precipitate, and converting the alkaline-earth salt of the (6S)-folinic into an alkali salt thereof.

17. A process for preparing an alkaline-earth salt of (6S)-folinic acid comprising crystallizing an alkaline-earth salt of (6R,S)-folinic acid at a pH between 9.0 and 12 to form a precipitate selectively enriched in said alkaline-earth salt of (6S)-folinic acid as compared to the concentration of an alkaline-earth salt of (6R)-folinic acid in said precipitate, and wherein the crystallization is carried out in the presence of excess of the same alkaline-earth ions employed to produce the alkaline earth salt.

* * * * *